United States Patent [19]
Klopotek

[11] Patent Number: 5,473,392
[45] Date of Patent: Dec. 5, 1995

[54] METHOD AND SYSTEM FOR TOPOGRAPHIC MEASUREMENT

[75] Inventor: Peter J. Klopotek, Framingham, Mass.

[73] Assignee: Summit Technology, Inc., Waltham, Mass.

[21] Appl. No.: 877,651

[22] Filed: May 1, 1992

[51] Int. Cl.$^6$ ........................................................ A61B 3/10
[52] U.S. Cl. .......................... 351/205; 351/212; 351/213; 351/214; 351/246; 351/221
[58] Field of Search .................................... 351/205, 212, 351/213, 214, 219, 221, 246

[56] References Cited

U.S. PATENT DOCUMENTS

| | | | |
|---|---|---|---|
| 2,250,521 | 7/1941 | Boeder | 351/247 |
| 3,108,523 | 10/1963 | Nuchman et al. | 351/212 |
| 4,120,585 | 10/1978 | DePalma . | |
| 4,309,085 | 1/1982 | Morrisson | 351/35 |
| 4,692,003 | 9/1987 | Adachi et al. | 351/212 |
| 4,761,071 | 8/1988 | Baron | 351/212 |
| 4,838,679 | 6/1989 | Bille | 351/221 |
| 4,852,987 | 8/1989 | Lohmann | 351/221 |
| 4,995,716 | 2/1991 | Warnicki et al. | 351/212 |
| 5,116,115 | 5/1992 | Lange et al. | 351/212 |
| 5,159,361 | 10/1992 | Cambier et al. | 351/212 |

OTHER PUBLICATIONS

Hage, "A Computerized Corneal Topographer for Us in Refractive Surgery", Refractive & Corneal Surgery, vol. 5, pp. 418–423; Nov./Dec. 1989.

Arffa et al., "Corneal Topography Using Rasterstereography" Refractive & Corneal Surgery; vol. 5; Nov.–Dec. 1989, pp. 414–417.

Steven R. Lange et al., "Intraoperative Corneal Topographic Measurement Using Phase–Shifted Projected Fringe Contouring", Ophthalmic and Visual Topical Meeting, Santa Fe, Minn., Jan. 1992, pp. 28–31.

Warnicki et al., "Corneal topography using computer analyzed rasterstereographic images", Applied Optics, vol. 27, No. 6, Mar. 15, 1988, pp. 1135–1139.

Harding, "Current State–of–the–Art of Contouring Techniques in Manufacturing", Journal of Laser Applications, Summer/Fall 1990, pp. 41–47.

Blatt et al., "Video Applications to Moire Metrology", Journal of Laser Applications, Summer/Fall 1990, pp. 35–40.

Wilson et al., "Accuracy and Precision of the Corneal Analysis System and the Topographic Modeling System", Department of Ophthalmology, University of Texas Southwestern Medical Center, Dallas, Tex., 1992; pp. 28–35.

"Par Technology Corporation catalog, Corneal Topography System".

VO Visioptic, Inc. catalog, EH–270 Computerized Corneal Topographer.

Primary Examiner—Ricky D. Shafer
Attorney, Agent, or Firm—Fish & Richardson

[57] ABSTRACT

The invention is a system and method of measuring the shape of a surface. The corneal topographer specifically shown comprises a transparent rigid reference member having a reference surface of a predetermined shape, a conformable substance capable of assuming the conformation of surfaces being pressed against, a light source for irradiating the conformable substance pressed between the reference surface and the corneal surface, and a detection system for detecting light propagating from the reference member and carrying information about the thickness. Two specific designs are shown, both based on differential topography. The first design uses a fluorescent conformable substance which fills the space between the reference surface and the corneal surface. The local intensity of fluorescent radiation detected by the detection system is correlated to the local thickness of the fluorescent conformable substance. The second design utilizes an absorbing conformable substance with a diffusive reflecting surface forming the section of the conformable substance pressed against the corneal surface during the measurement process. The local thickness of the absorbing conformable substance is determined from the amount of light locally absorbed. A topographer of the first or the second design can be used to measure the topography of the surface of a solid object of various constructions without regard to the finish of the surface, e.g., specular reflective, diffusely reflective or non-reflective.

23 Claims, 7 Drawing Sheets

1

METHOD AND SYSTEM FOR TOPOGRAPHIC MEASUREMENT

BACKGROUND OF THE INVENTION

This invention relates to measuring the shape of surfaces. Whereas other uses can be envisioned, the invention has particular applicability to measurement of the corneal surface and to facilitating treatments of the eye.

Corneal topography measurements are valuable for planning, performing, and evaluating the effects of surgical procedures. Measurements of the corneal surface are needed for keratorefractive procedures, which correct a refractive power of the eye by changing the curvature of the corneal surface. In addition, corneal topography can also be used to predict the results of radial keratotomy, evaluate the design of epikeratophakia for myopia, diagnose the stage of keratoconus, and guide suture removal following corneal transplantation.

There are several methods to test and characterize the optical power of the eye and the cornea in particular. One of the oldest methods is the Snellis diagram test, therein a patient is asked to read letters or to recognize shapes from a standard distance. This is a subjective method which requires the patient's cooperation.

Since the corneal curvature and its dioptric power account for about three quarters of the refractive power of the eye, it is important, however, to measure the corneal surface with greater accuracy than the Snellis diagram test provides.

One class of methods of measuring the corneal surface is based on the deflectometry principle, which utilizes reflection of light from the smooth corneal tear film (i.e., the lower, oily part of the tear film). In this method, a system of rings is optically projected onto the surface of the eye. A doctor directly observes the symmetry of the reflected rings and judges the condition of the eye. This qualitative technique is quite reliable; however, it is dependent upon the doctor's experience.

In recent years, automatic measurement devices which measure the shiny surface of the cornea using deflectometry have been introduced. These are computerized systems which analyze distortion of the images of a system of rings optically projected towards the eye and detected by a camera detection system. The spatially defined system of rings is projected onto the smooth eye surface from a precisely positioned source governed by a computer. The reflected pattern is detected by a camera and stored in the memory of a computer. Using the well-defined characteristics of the incident and detected light, the geometric position of the source and the detector, and the shapes of the incident and detected pattern the computer calculates the shape of the reflecting sphere.

Such a computerized topographer can be used as a principal guide in a laser system performing corneal sculpturing surgery, to provide the necessary pre-operative and post-operative corneal measurements, or to provide the measurements to guide post-operative manipulation of the cornea for reduction of astigmatism. However, during and after eye surgery, once the epithelium is removed from the eye surface, the local microtopology of the eye surface has changed so that the surface of the eye is only partially a specular reflector, and now partially a diffuse reflector. Since a diffuse reflector has no fixed relationship between the incident angle and the reflected angle of the projected light, the described deflectometry-based topographer is no longer useful. Furthermore, since both the corneal topographer using deflectometry and a laser beam delivery system of a laser sculpturing system require positioning on the optical axis of the eye, there is difficulty in incorporating both systems into one unit designed for intraoperative use. In addition, since the vision of a patient during surgery or after de-epithelization is significantly impaired, it is difficult to achieve proper eye alignment necessary for deflectometric measurement.

Rasterography or fringe phase shifts are methods of determining topography of the cornea which are well suited for diffusive surfaces. The method does not require smooth reflective surfaces and images can be obtained on surfaces with some degree of epithelial irregularity. The methods use an optical pattern, for example, a grid of vertical and horizontal bars of light projected onto the corneal surface. The projected pattern has very well established characteristics including shape, regularity, and separation of the points. A detection system registers and analyzes the deformation of the detected pattern. A computer analyses the deformation data and establishes the topography of the measured surface. The detection system can be located in any place since it detects the light from a diffused reflector which reflects light in all directions. The advantage of this method is that the projected image can cover the entire cornea including the central visual access, far periphery, and limbus, interpalpebral conjunctiva, and lid margins. This technique, however, is not useful for smooth, shiny surfaces, such as the epithelium surface.

There are other optical methods such as confocal microscopy, shared interferometry, infrared interferometry and multi-color interferometry that can be used to characterize the eye surface but each has its limitations and fails to meet fully, for instance, the needs in the case of laser sculpting of the cornea.

Again, as suggested above, in laser sculpting of the cornea, the devices based on deflectometry are well tailored to measure the specular type surface which is the surface of the eye during the initial stages of laser sculpting procedures, and devices based on rasterography are well suited to measure diffuse type corneal surface which occurs after laser sculpturing of the corneal surface was performed, but presently, there are no entirely satisfactory devices which can precisely measure both types of surfaces, and particular surface which in part are of one type and in part another. Neither are there devices which can be conveniently integrated into surgical laser systems. Furthermore, some of the previously mentioned instruments require a patient's cooperation since he or she needs to look in some specific direction.

In general, the discussed topographers are based on the assumption that the cornea has a conic surface i.e. a sphere, an ellipse, a parabola, or a hyperbola, but in reality, the living cornea is none of these; it is an aspheric section with great individual variation, and hence most of the known techniques are not completely accurate.

SUMMARY OF THE INVENTION

According to one aspect of the invention, in laser sculpting of the cornea, the surgeon is informed of the starting profile of the corneal surface and the surface changes during and after the procedure by a single instrument which avoids disadvantages of prior instruments. Advantageous by such a corneal topographer is incorporated into the laser sculpting device itself.

The invention provides a fully automatic corneal topographer which does not rely upon postulation of any corneal surface. Topographers according to the invention are suitable for incorporation into a laser sculpturing system and can reliably measure both specular and diffuse types of surfaces, without requiring significant cooperation of the patient during the measurement procedure.

According to one important aspect of the invention, a system for determining information concerning the topography of a portion of the exterior surface of the eye is provided, the system comprising a rigid reference member having a reference surface of predetermined shape, the reference surface being positionable in close proximity to and directed toward the exterior surface of the eye, a conformable substance capable of assuming the conformation of surfaces against which it is engaged and adapted to fill the space between the surface of the eye and said reference surface of the reference member to conform to the respective surfaces, means for determining thickness data regarding the conformed substance filling the space over a multiplicity of data points sufficient in number and spacing to represent the desired information concerning the topography of the surface of the eye, and means for determining the desired information concerning the topography of the surface of the eye from the thickness data in reference to said predetermined shape of said reference surface.

Preferred embodiments of this aspect of the invention have one or more of the following features.

The reference surface of the rigid reference member is concavely shaped to approximate the surface of the eye to enable the conformable substance to have a thin cross section over the examined portion of the eye, enabling small differences in topography of the eye surface to be detected as relatively large percentage changes in the thickness of the cross-section. The conformable substance comprises a fluid contained by a pliable barrier film supported on the reference member in a manner to confine the fluid, the film having a surface exposed to the eye that is defined by a biologically compatible substance. The reference surface is concave and substantially spherical with a radius of about 8 millimeters. The conformable substance contains a constituent which fluoresces when illuminated by selected radiation such that the intensity of fluorescent emission from points in the substance are dependent upon the thickness of the conformable substance at the points, the system further comprising the reference member being transparent to radiation; a radiation source positioned and adapted to irradiate the conformable substance, when conformed to the surface of the eye and the reference surface, with radiation passing through the reference member; and a detector for detecting the intensity of fluorescent radiation emitted from a multiplicity of points distributed over the conformable substance sufficiently to represent the information concerning the topography of the surface of interest, the fluorescent radiation passing through the reference member, the intensities being dependent upon the thickness of the fluorescent material at the respective points and constituting said thickness data; preferably in this case the conformable substance comprises a biologically compatible liquid carrying a biologically compatible fluorescent constituent, confined by a biologically compatible barrier film exposed to engage the eye.

As an alternative, the conformable substance comprises a constituent which substantially absorbs radiation passing through the reference member and is contained within a pliable barrier having a surface exposed to the eye formed by a diffusive reflector that produces diffused radiation when illuminated; preferably in this case, the reference member is transparent to selected radiation and the conformable substance substantially absorbs the radiation such that the intensity of diffusively reflected radiation from points in the pliable barrier pressed against the surface of the eye are dependent upon the thickness of the conformable substance at the points, the system further comprising a radiation source positioned and adapted to irradiate the conformable substance, when conformed to the surface of the eye and the reference surface, with incoming radiation and diffusely reflected radiation passing through the reference member, and a detector for detecting the intensity of diffuse radiation from a multiplicity of points distributed over the pliable barrier sufficient to represent the information concerning the topography of the surface of interest, the intensities dependent upon the thickness of the conformable substance at the respective points and constituting said thickness data.

Any of the systems described above may have one or more of the following features. The detector comprises a camera sensitive to radiation received from the reference member. Means are provided for forming an image of detected radiation received via the reference member and determining energy intensities at points in the image. A filter is provided for selecting the wavelength of the radiation detected by the detector. Means are provided to digitize signals of the intensities to obtain the thickness data and computer means for analyzing the data, preferably in which the computer means being adapted to fit the digitized thickness data to a polynomial, the polynomial containing a low order terms representing translational displacements, offset, and angular tilting of the rigid reference member relative to said eye surface, the polynomial also containing higher-order terms representing information about the topography of the eye and the computer means adapted to eliminate the zero order and first order terms.

The detector comprises a lens for receiving radiation through the reference member, a camera upon which the lens focusses an image of the radiation, the camera adapted to produce analog intensity signals, and a frame grabber for producing digital signals from the analog signal for computer analysis.

The system includes means to digitize the thickness data, means to provide a thickness data polynomial by fitting the digitized data to a polynomial, means to provide detailed data of the reference surface, and means to combine the thickness data polynomial with the reference surface topography to provide information about the topography of the eye.

According to another aspect of the invention, a system is provided for determining information concerning the topography of the surface of an object, in general, comprising a rigid reference member having a reference surface directed toward the object, the reference surface being of predetermined shape and the reference member being transparent to radiation, a conformable substance capable of assuming the conformation of surfaces against which it is engaged, the conformable substance comprising a constituent which fluoresces when illuminated by radiation passing through the reference member, such that the intensity of fluorescent emissions from points in the substance are dependent upon the thickness of the substance at the points, means for pressing the rigid reference member relatively against the surface of the object in the manner that the conformable substance conforms, on one side, to the surface of the object, and on the other side to the reference surface of the reference member, a radiation source for irradiating the conformable substance, when conformed to the object and the reference surface with radiation passing through the reference member, a detector for detecting the intensity of fluorescent radiation emitted from a multiplicity of points in the conformable substance sufficient to represent desired information concerning the topography of the surface of interest, the detector receiving radiation from the conformable substance through the reference member, and means for determining the topography of the surface of the object from the thickness data in reference to the predetermined shape of the reference surface.

According to another aspect of the invention, a system is provided for determining information concerning the topography of the surface of an object, in general, comprising a rigid reference member having a reference surface directed toward the object, the reference surface being of predetermined shape and the reference member being transparent to radiation, a conformable substance capable of assuming the conformation of surfaces against which it is engaged, the conformable substance comprising a constituent which substantially absorbs radiation, the constituent being contained within a pliable barrier having a surface exposed to the surface of the object, the barrier being formed by a diffusive reflector, means for pressing the rigid reference member relatively against the surface of the object in the manner that the conformable substance conforms, on one side, to the surface of the object, and on the other side to the reference surface of the reference member, a radiation source for irradiating the conformable substance, when conformed to the surface of the object and the reference surface with radiation passing through the reference member, a detector for detecting the intensity of diffuse radiation from a multiplicity of points distributed over the pliable barrier sufficient to represent desired information concerning the topography of the surface of interest, the detector receiving radiation from the multiplicity of points through the reference member, intensities of the detected radiation being dependent upon the thickness of the conformable substance at the respective points and constituting the thickness data, and means for determining the topography of the surface of the object from said thickness data in reference to the predetermined shape of said reference surface.

Other aspects of the invention are methods performing the functions of the systems described above. Other advantages and features of the invention will be apparent from the following description and from the claims.

DESCRIPTION OF THE PREFERRED EMBODIMENTS

Figure 1:
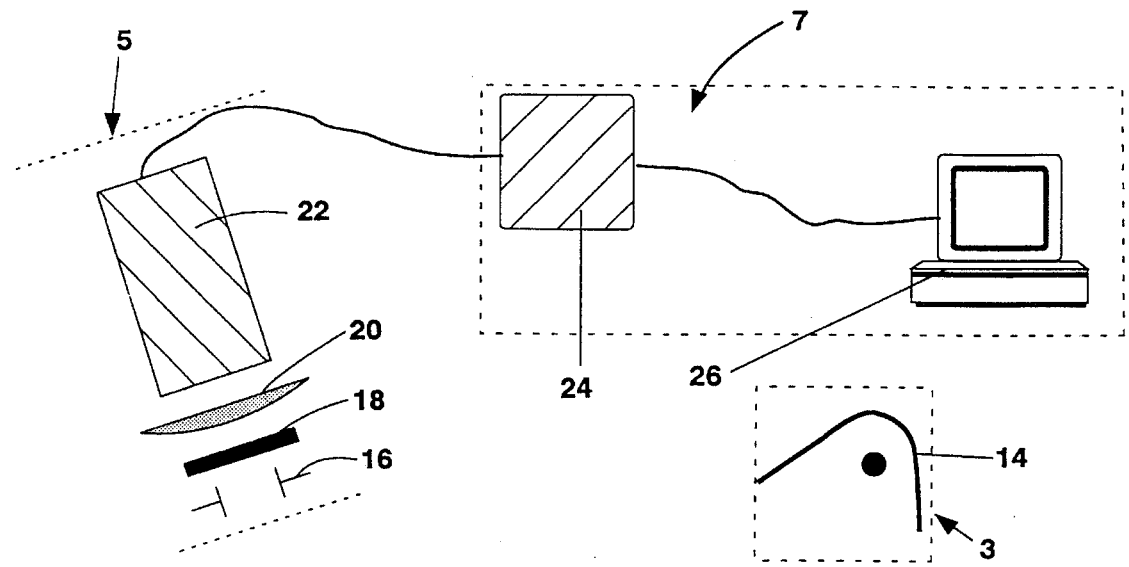
FIG. 1 is a diagrammatic view of a corneal topographer embodying the invention.
Figure 1:
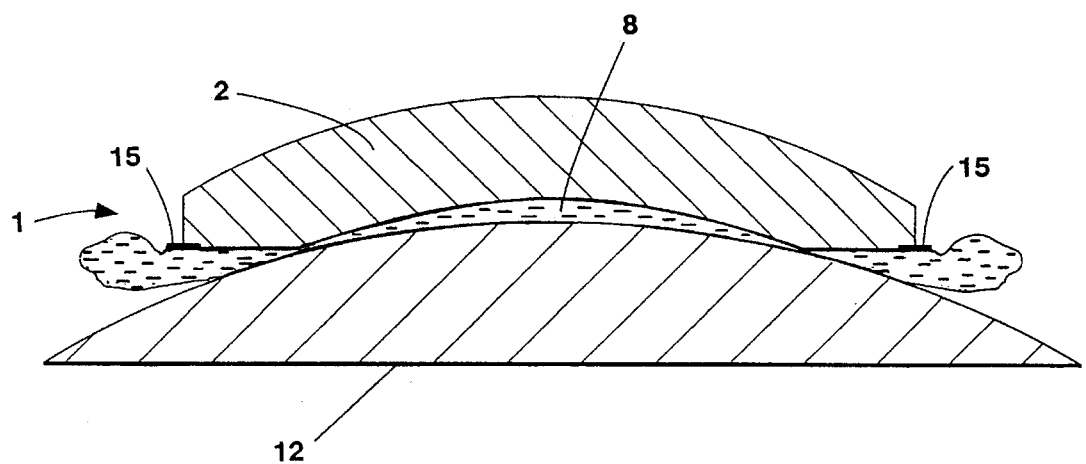
Figure 2:
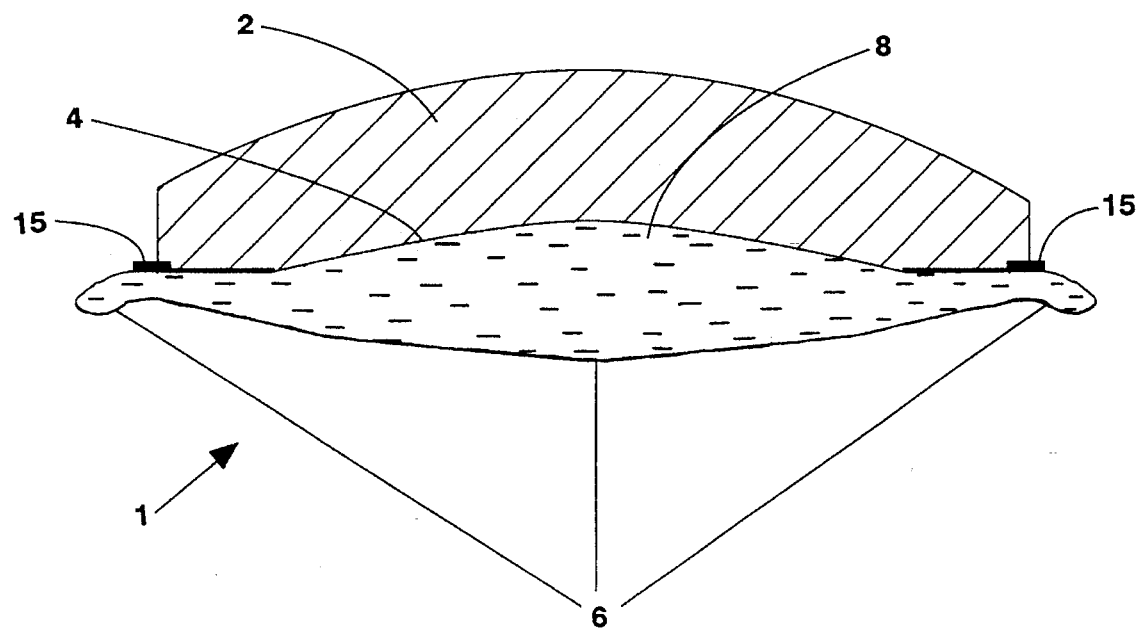
FIG. 2 is a diagrammatic view of an eye contact system according to the invention.

Referring to FIG. 1, a corneal topographer of the first embodiment comprises an eye contact system 1, a detection system 5, a light source 3, and a computer system 7. Referring to FIG. 2, eye contact system 1 comprises a rigid reference member 2 made of a transparent material. Reference member 2 has a rigid concavely shaped reference surface 4 of predetermined curvature which conforms to the gross contour expected of eyes. A pliable fluid impermeable conforming membrane 6 is attached to reference member 2 below surface 4 using a fastener ring 15. Membrane 6 confines a dye-containing fluid 8 below reference 4. A fluid reservoir and a small pump, not shown in FIG. 2, can be connected to conforming membrane 6 to vary the amount of fluid present. Conforming membrane 6, while confining the fluid, assumes the shape of a surface it is pressed against.

FIG. 1 shows eye contact system 1 pressed against the corneal surface 12. The pliable membrane 6 and the dye-containing fluid 8 enclosed inside are pressed between rigid reference member 2 and corneal surface 12 so that the space between reference surface 4 and the actual surface of the eye is filled with the dye-containing fluid. The excess fluid and dye are shown present on the sides of rigid reference member 2 within conforming membrane 6. The shape of reference surface 4 approximates the corneal curvature, and thus the amount of the dye-containing fluid located between the two surfaces is very small and of shallow depth. Reference surface 4 is preferably made of a wettable material in order to always fill the space between the two surfaces when eye contact system 1 is applied to the corneal surface 12.

Referring to FIG. 1, detection system 5 contains an adjustable iris 16 for regulating the optical light exposure to a camera 22. The incoming light from reference member 2 is focused by an imaging lens 20 after it is filtered by a wavelength selective filter 18. The filter 18 functions to separate the wavelength of the light of interest from the total incoming light passing through iris 16. The detected signal is processed by a frame grabber and a digitizer 24 connected to camera 22 and is input to a computer 26. Computer 26 is used to analyze and store the digitized signal.

Figure 3:
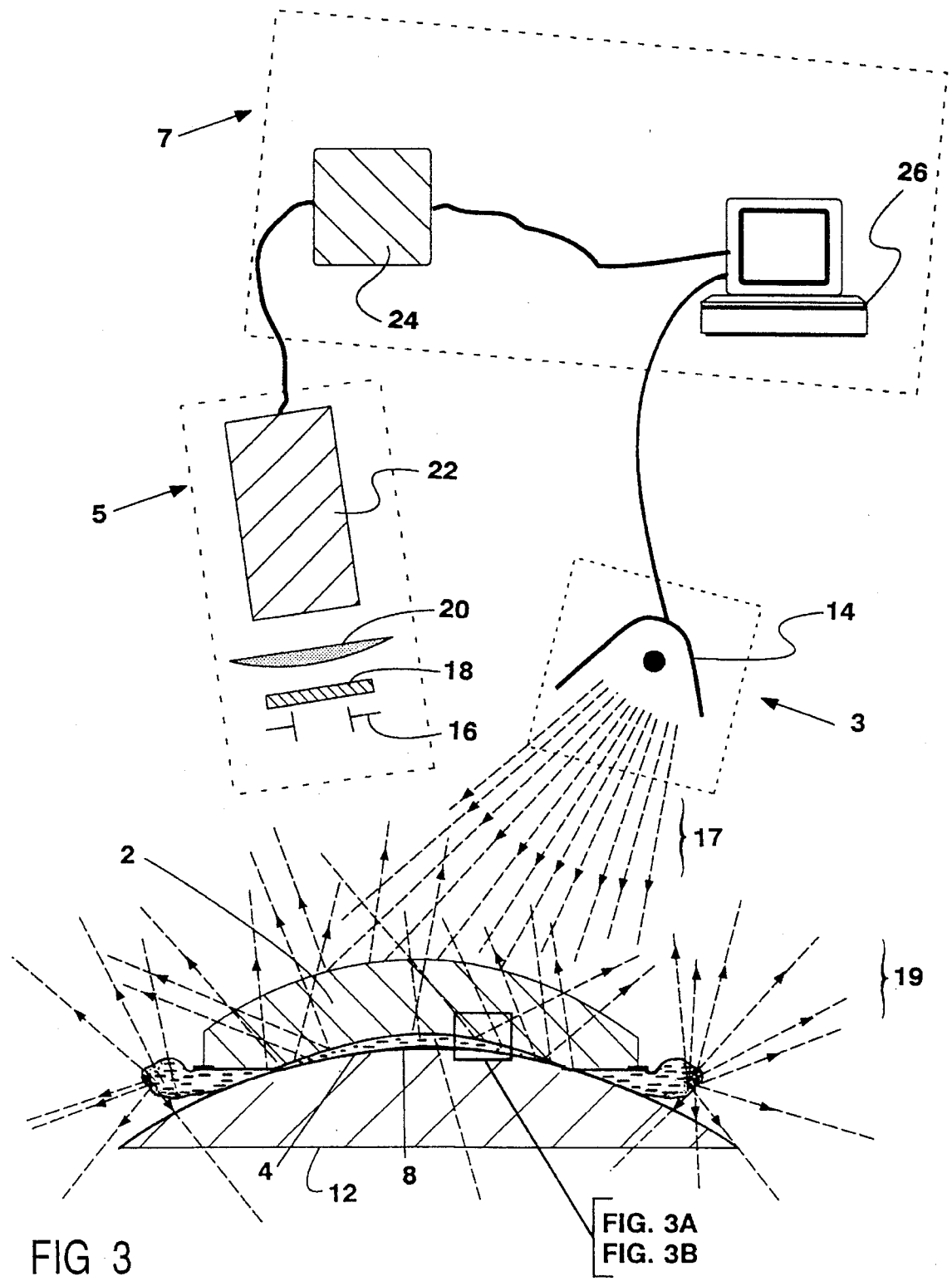
FIG. 3 is a diagrammatic view of the operation of the corneal topographer for two preferred embodiments of the invention.
Figure 3A:
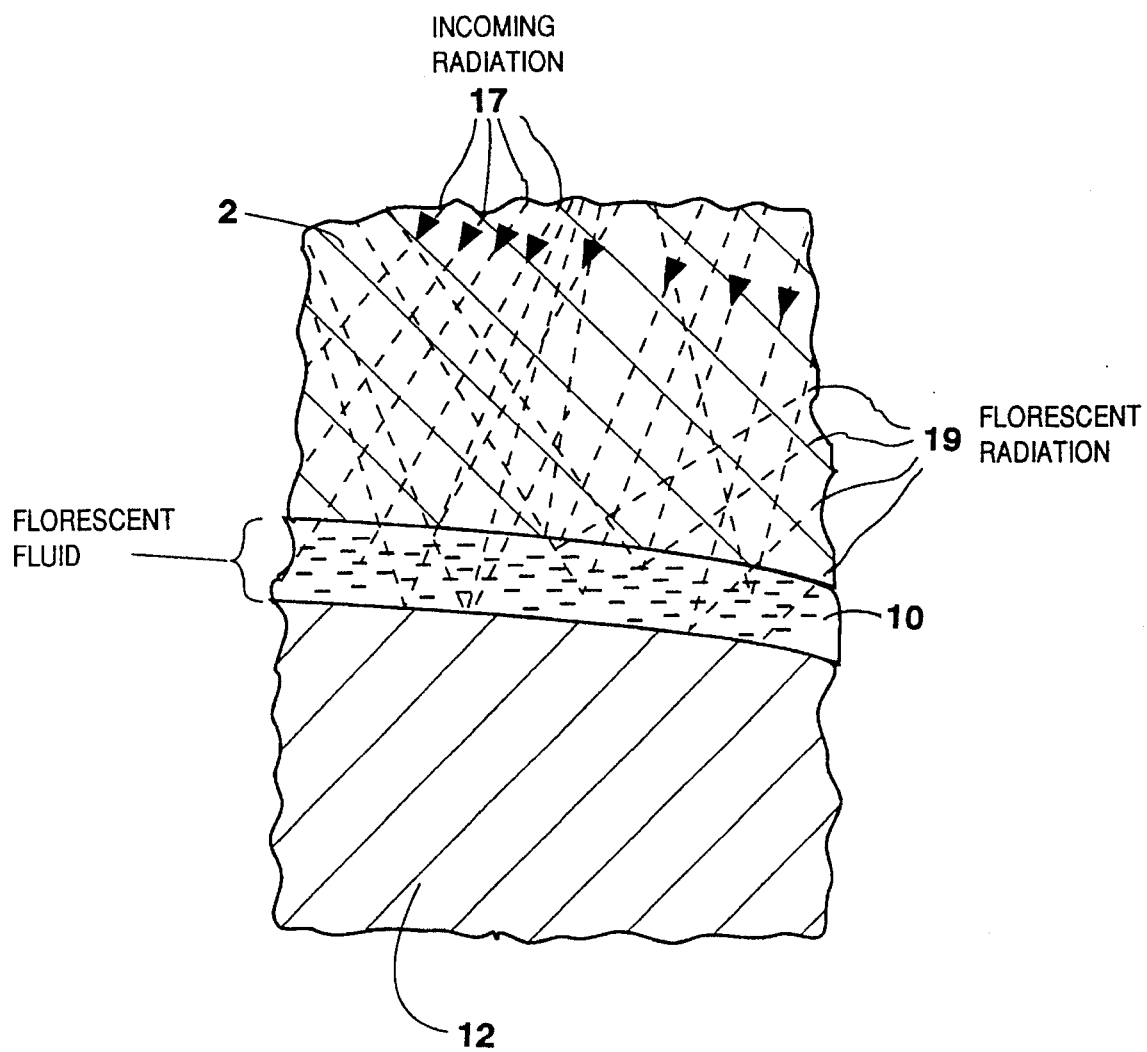
FIG. 3a is an enlarged section of FIG. 3 diagrammatically showing the first preferred embodiment using fluorescent measurements.

The first preferred embodiment of the invention is a topographer using a differential method of measuring topography by detecting fluorescent radiation. The fluorescent material is a fluorescing constituent which is totally mixed with fluid 8 and confined within conforming membrane 6. Referring to FIG. 3, light source 14 irradiates eye contact system 1, and the incoming radiation passes through transparent rigid reference member 2. The radiation 17 reaches the fluid 8 confined between unknown eye surface 12 and known reference surface 4 of reference member 2. The fluorescing fluid is activated by the incident light and emits fluorescent radiation 19. This is diagrammatically shown in FIG. 3a. A portion of the emitted fluorescent radiation passes outwardly through rigid reference member 2 and is detected by detector 22.

As mentioned above, the thickness of the fluorescing fluid filling the space between the two surfaces is very small and varies locally with slight differences between the surfaces. The local thickness of this fluid contains information about the corneal surface. The intensity of the fluorescent light radiated by the fluorescent dye depends, at any point on the thickness of the fluorescent dye contained between the two surfaces. Referring to FIG. 3, detecting system 5 detects fluorescent radiation focused by imaging lens 20 onto camera 22. Filter 18 permits passage only of the fluorescent light and blocks other incoming light entering through iris 16. The detected signal is then digitized by digitizer 24 and stored in the memory of computer 26. The whole measurement process is controlled by the computer 26, which also stores the known source-detector geometry, the shape of reference surface 4, properties of the incident light 17 and of the emitted light 19.

Figure 3B:
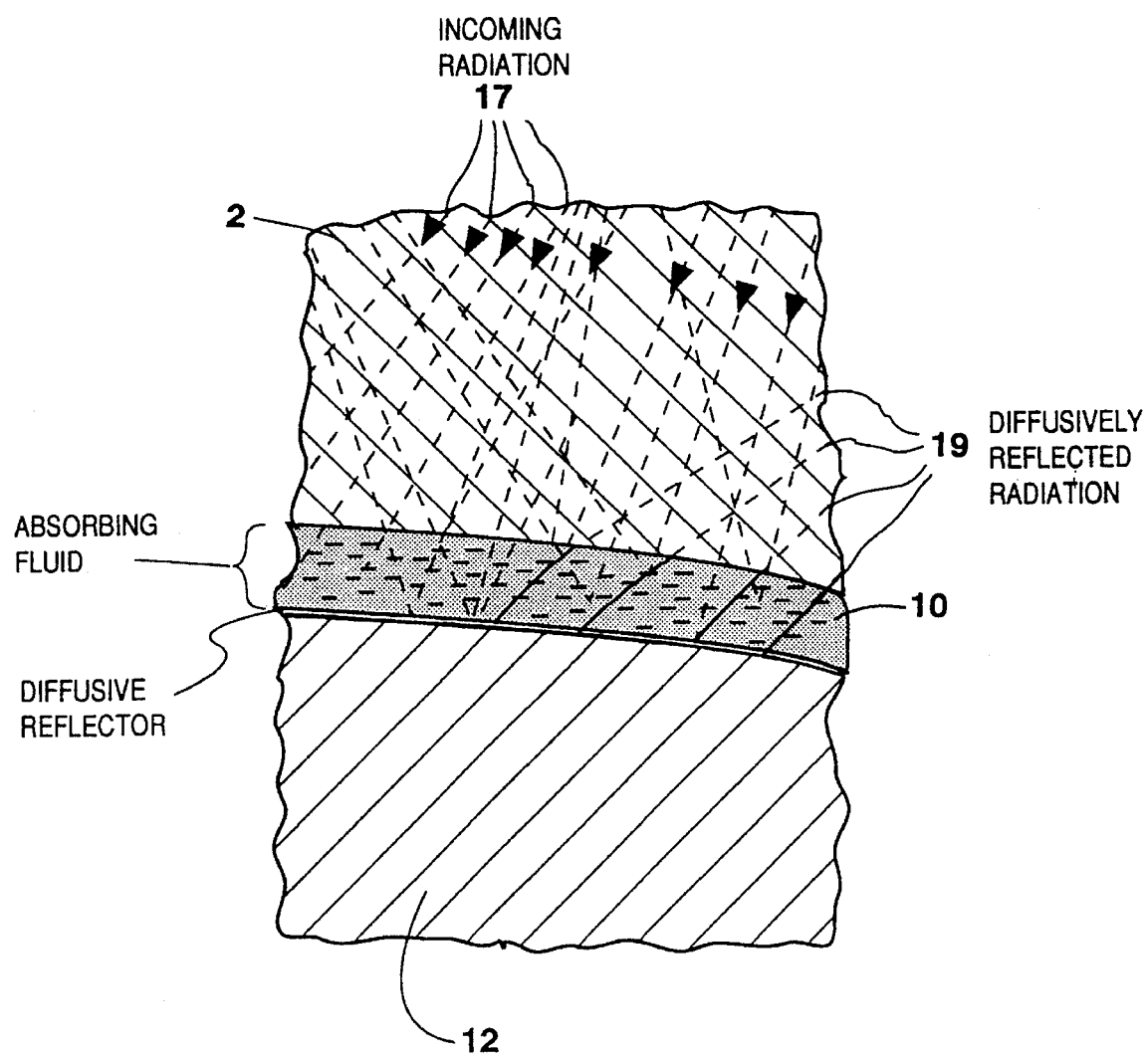
FIG. 3b is an enlarged section of FIG. 3 diagrammatically showing the second preferred embodiment using absorption measurements.

The second preferred embodiment of the invention is a topographer of similar construction using a differential method of measuring topography by detecting localized absorption of light. The absorbing material is an absorbing constituent which is totally mixed with fluid 8. The absorbing fluid is again confined by pliable conforming membrane 6. In this embodiment, the section of the conforming membrane exposed to the corneal surface 12 comprises a diffusive optical scatterer (for example, Teflon®) and the other sections are made of non-reflecting material. In the measurement process, referring to FIG. 3, eye contact system 1 is pressed against corneal surface 12. Light source 14 irradiates eye contact system 1. The incoming light passes through transparent rigid reference member 2, the absorbing fluid, and that incoming light 17 which is not absorbed by the fluid reaches the diffuser section of the conforming membrane 6. As shown in FIG. 3b, a fraction of light is diffusely reflected and travels back through the absorbing fluid, thence through transparent reference member 2 and is detected by detection system 5. The geometry of source 14, the known shape of reference surface 4, eye contact system 1, and detection system 5 are stored in the memory of computer 26. The light detected by detection system 5 passes twice through the thickness of absorbing fluid confined between known reference surface 4 and the unknown corneal surface 12. The local attenuation of reflected light 19 depends, here again on the local thickness of the absorbing fluid, and thus the local intensity of the detected light possesses the desired information about the thickness of the absorbing fluid of each respective point over the surface of the cornea.

Referring to both preferred embodiments, the system performs differential thickness measurements. At any instant of time, camera 22 of detection system 5 detects intensity of radiation arriving from a point which is located between the measured corneal surface and known reference surface 12. This intensity of the fluorescent or diffusively reflected radiation is dependent on the local thickness of the mixture of fluids compressed between the two surfaces at that point. The detection system scans an area of approximately 5 mm² of reference member 2 and forms a large number of adjacent pixels (surface regions of the smallest resolution) containing the intensity information for the related locations. Digitizer 24 digitizes the detected intensities, and stores the three dimensional sets into the memory of computer 26. Each pixel has x,y coordinates and a thickness value computed from the intensity of the detected radiation. The x,y resolution of the system of a preferred embodiment is about 50 µm.

From this data, with suitable compensation for the selected geometry of the system, computer 26 creates a model of the detected thickness, and incorporate to the model the curvature of reference surface 4 to create a model of the measured corneal surface. This is preferably performed by fitting the detected data to a two dimensional polynomial and adding the resulting topography to the topography of the rigid reference surface 4. The resulting topography represents the measured corneal surface. This differential topography measurement can have resolution of a few micrometers.

Figure 4A:
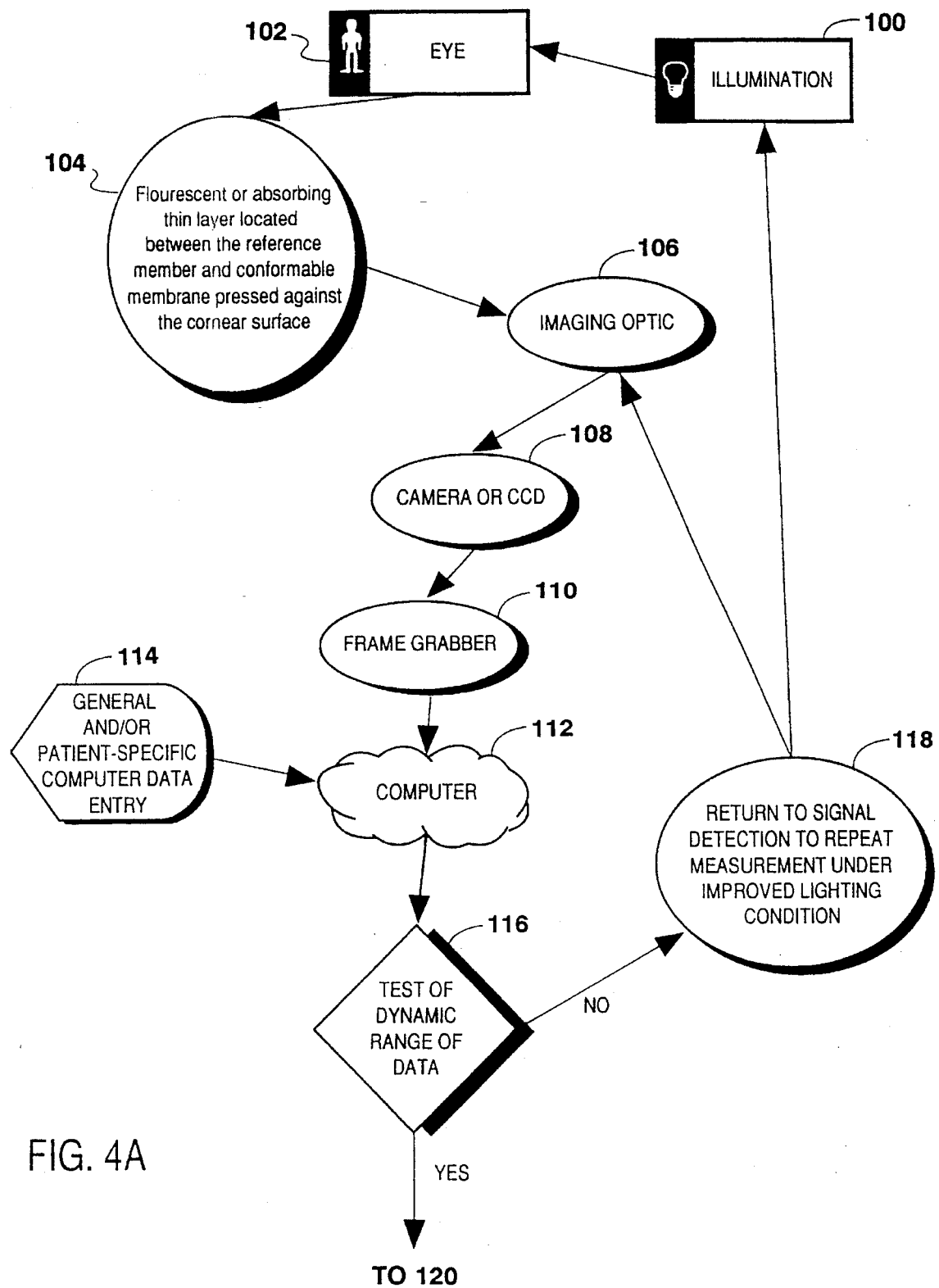
FIG. 4a and 4b are flow diagrams describing the operation of topographers.
Figure 4B:
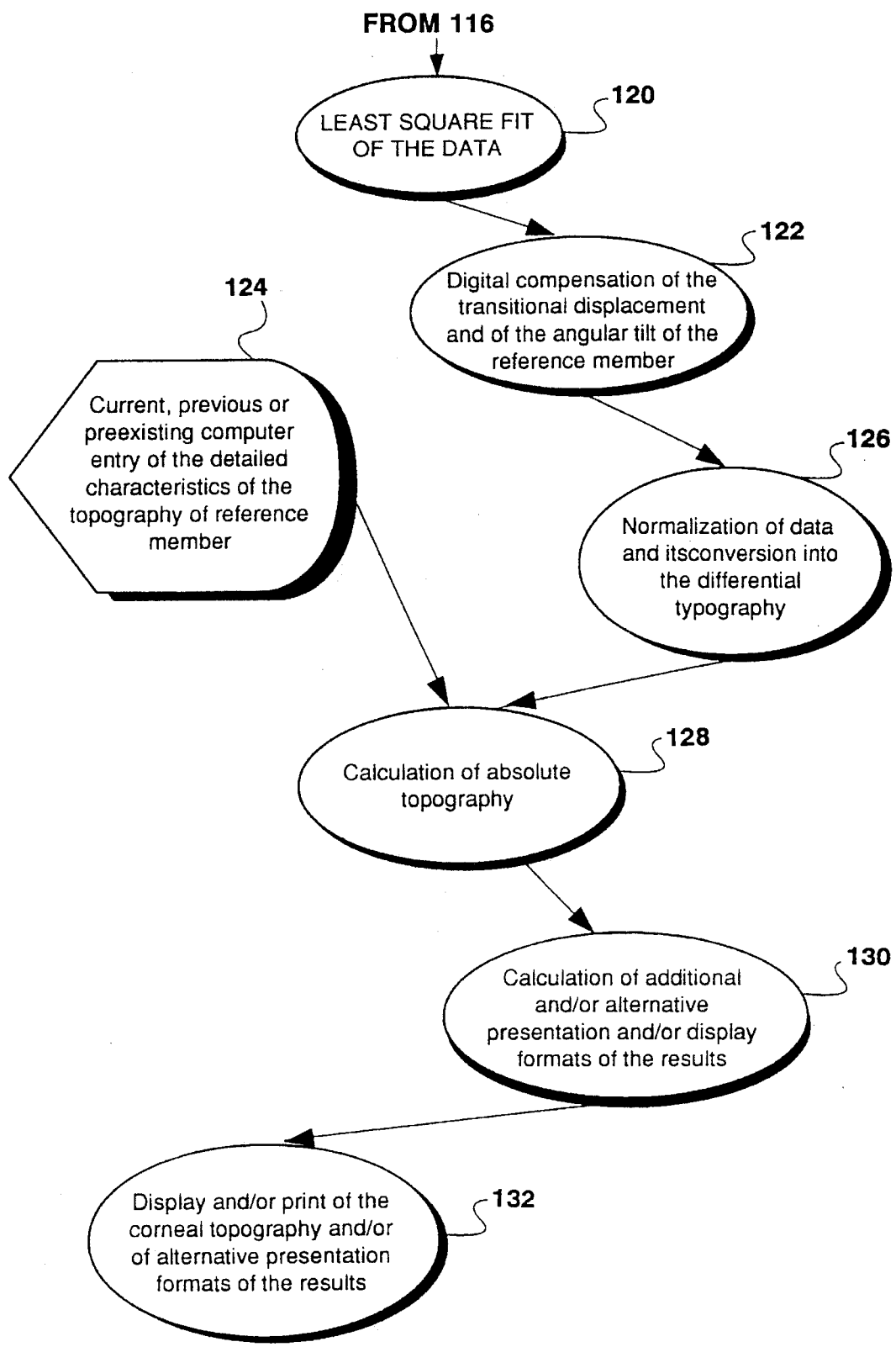

FIGS. 4a and 4b schematically show the operation of the topographer. Referring also to FIG. 1, rigid transparent reference member 2 with conformable membrane 13 containing a fluorescent (or absorbing) fluid is pressed against the corneal surface (104). The light source 3 directs light 17 onto reference member 2. The imaging system 106 focusses returning signal 19 onto camera 22, or in FIG. 4a, camera or CCD 108. In steps 108, 110, and 112, the returning light is detected, digitized and saved frame-by-frame in the memory of computer 26 (112 in FIG. 4a). The computer governs the whole process, receives general and/or patient specific data (114), tests the detected data (116) and rejects unreliable data. If the dynamic range of the signal is wrong, the computer initiates another measurement under improved lighting conditions (118). The computer performs fitting of the data (120). The fitted data are manipulated to eliminate errors caused by translational displacement or an angular tilt (122). Then, the topography data (126) are compared to the reference topography data (124) that represent reference surface 4 and the corneal topography is determined (128). The calculation can also take into account patient specific data, for example, previous corneal topography measurements. The corneal topography is then displayed (132).

The topographer can be a separate system or can be incorporated into a surgical system to provide measurements of the corneal surface during corneal surgery. During an eye operation it is useful to establish a reference point on the surface of the eye. This point is needed to compare the shape of the surface before and after surgery. This can be done by marking a specific point which will be kept for the duration of the operation. The marking would be done using a dye and placing a dot on the eye surface. This will help the surgeon to know the proper orientation of the eye.

During an eye operation the eye are anesthetized, thus the patient will not feel any discomfort when reference member 2 is pressed to the eye surface. However, when the corneal topographer is used as a stand-alone unit, some patients might feel discomfort or pain when the reference member is applied to the eye surface. In these cases, the eye will be anesthetized before the reference member is applied.

What is claimed is:

1. A system for determining information concerning the topography of a portion of interest of the exterior surface of an eye, the system comprising:

(a) a reference member having a rigid reference surface of predetermined shape; said reference surface being positionable in close proximity to and directed toward the exterior surface of the eye, (b) a conformable substance capable of assuming conformation of surfaces against which it is engaged and adapted to fill the space between said surface of the eye and said reference surface of said reference member to conform to the respective surfaces, said conformable substance comprises a biologically compatible liquid carrying a biologically compatible fluorescent constituent, Confined by a biologically compatibles, pliable barrier exposed to engage the eye, (c) means for determining thickness data regarding said conformed substance filling said space over a multiplicity of data points sufficient in number and spacing to represent desired information concerning the topography of the surface of the eye, and (d) means for determining the desired information concerning the topography of said surface of the eye from said thickness data in reference to said predetermined shape of said reference surface.

2. The system of claim 1 wherein said constituent which fluoresces when illuminated by selected radiation such that intensity of fluorescent emission from points in said substance are dependent upon the thickness of said conformable substance at said points, said system further comprising (a) the reference member being transparent to radiation, (b) a radiation source positioned and adapted to irradiate said conformable substance, when conformed to the surface of the eye and said reference surface, with radiation passing through said reference member, and (c) a detector for detecting the intensity of fluorescent radiation emitted from a multiplicity of points distributed over said conformable substance sufficiently to represent the information concerning the topography of said portion of interest, the fluorescent radiation passing through said reference member, the intensities of the fluorescent radiation being dependent upon the thickness of said fluorescent substance at the respective points and constituting said thickness data.

3. A system for determining information concerning the topography of a portion of interest of the exterior surface of an eye, the system comprising:

(a) a reference member having a rigid reference surface of predetermined shape; said reference surface being positionable in close proximity to and directed toward the exterior surface of the eye, (b) a conformable substance capable of assuming conformation of surfaces against which it is engaged and adapted to fill the space between said surface of the eye and said reference surface of said reference member to conform to the respective surfaces, said conformable substance comprises a constituent which substantially absorbs radiation passing through the reference member and is contained within a pliable barrier having a surface exposed to the eye formed by a diffusive reflector that produces diffused radiation when illuminated, (c) means for determining thickness data regarding said conformed substance filling said space over a multiplicity of data points sufficient in number and spacing to represent desired information concerning the topography of the surface of the eye, and (d) means for determining the desired information concerning the topography of said surface of the eye from said thickness data in reference to said predetermined shape of said reference surface.

4. The system of claim 3 wherein said reference member is transparent to selected radiation and said conformable substance substantially absorbs said radiation such that intensity of diffusively reflected radiation from points in said pliable barrier pressed against the surface of the eye are dependent upon the thickness of said conformable substance at said points, said system further comprising (a) a radiation source positioned and adapted to irradiate said conformable substance, when conformed to the surface of the eye and said reference surface, with incoming radiation and diffusely reflected radiation passing through said reference member, and (b) a detector for detecting the intensity of diffuse radiation from a multiplicity of points distributed over said pliable barrier sufficient to represent the information concerning the topography of said portion of interest, said intensities dependent upon the thickness of said conformable substance at the respective points and constituting said thickness data.

5. The system of claim 2 or 4 including means to digitize signals of said intensities to obtain the thickness data and computer means for analyzing the data.

6. The system of claim 5 in which the computer means being adapted to fit the digitized thickness data to a polynomial, said polynomial containing low order terms representing translational displacements, offset, and angular tilting of said reference member relative to said eye surface, said polynomial also containing higher-order terms representing information about the topography of the eye and said computer means adapted to eliminate the zero order and the first order terms.

7. The system of claim 2 or 4 wherein said detector comprises a camera sensitive to radiation received from said reference member.

8. The system of claim 2 or 4 including means for forming an image of detected radiation received via said reference member and for determining energy intensities at points in said image.

9. The system of claim 2 or 4 including a filter for selecting the wavelength of the radiation detected by said detector.

10. The system of claim 2 or 4 wherein said detector comprises a lens for receiving radiation through said reference member, a camera upon which the lens focusses an image of said radiation, said camera adapted to produce analog intensity signals, and a frame grabber for producing digital signals from said analog signals for computer analysis.

11. The system of claim 2 or 4 further comprising means for digitizing said thickness data, means for calculating a thickness data polynomial by fitting the digitized thickness data to a polynomial, means for providing detailed data of said reference surface, and means for combining said thickness data polynomial with said reference surface topography to provide information about the topography of the eye.

12. A system for determining information concerning the topography of a surface of interest of an object comprising (a) a reference member having a rigid reference surface directed toward said object, said reference surface being of predetermined shape and said reference member being transparent to radiation, (b) a conformable substance capable of assuming conformation of surfaces against which it is engaged, said conformable substance comprising a constituent which fluoresces when illuminated by radiation passing through said reference member, such that intensity of fluorescent emissions from points in said substance are dependent upon the thickness of said substance at said points, said conformable substance being attached to and movable with said reference member, (c) means for pressing said reference member relatively against the surface of said object in the manner that said conformable substance conforms, on one side, to the surface of said object, and on the other side to said reference surface of said reference member, (d) a radiation source for irradiating said conformable substance, when conformed to said object and said reference surface with radiation passing through said reference member, (e) a detector for detecting the intensity of fluorescent radiation emitted from a multiplicity of points in said conformable substance sufficient to represent desired information concerning the topography of the surface of interest, said detector receiving radiation from said conformable substance through said reference member, and (f) means for determining the topography of the surface of said object from thickness data of said conformable substance in reference to said predetermined shape of said reference surface.

13. A system for determining information concerning the topography of a surface of interest of an object comprising (a) a reference member having a rigid reference surface directed toward said object, said reference surface being of predetermined shape and said reference member being transparent to radiation, (b) a conformable substance capable of assuming conformation of surfaces against which it is engaged, said conformable substance comprising a constituent which substantially absorbs radiation, said constituent being contained within a pliable barrier having a surface exposed to the surface of said object, said barrier being formed by a diffusive reflector, (c) means for pressing said reference member relatively against the surface of said object in the manner that the conformable substance conforms, on one side, to the surface of said object, and on the other side to said reference surface of said reference member, (d) a radiation source for irradiating said conformable substance, when conformed to the surface of said object and said reference surface with radiation passing through said reference member, (e) a detector for detecting the intensity of diffuse radiation from a multiplicity of points distributed over said pliable barrier sufficient to represent desired information concerning the topography of the surface of interest, said detector receiving radiation from said multiplicity of points through said reference member, intensities of said detected radiation being dependent upon the thickness of said conformable substance at the respective points and constituting said thickness data, and (f) means for determining the topography of the surface of said object from thickness data of said conformable substance in reference to said predetermined shape of said reference surface.

14. A method for determining information concerning the topography of a portion of interest of the exterior surface of an eye comprising:

(a) providing a reference member having a reference surface of a predetermined shape; said reference surface being directed closely toward the exterior surface of the eye, (b) providing between said reference surface and the surface of the eye a conformable substance capable of assuming the conformation of surfaces against which it is pressed, said conformable substance being attached to and movable with said reference member, (c) holding said reference member stationary to the surface of the eye in the manner that the conformable substance fills the space and conforms, on one side, to the surface of the eye and, on the other side, to the reference surface of said reference member, (d) determining thickness data regarding the thickness of the resultant conformed substance over a multiplicity of data points sufficient in number and spacing to represent desired information concerning the topography of said portion of interest, and (e) determining the desired information concerning the topography of said portion of interest of the eye from said thickness data in reference to said predetermined shape of said reference surface.

15. The method of claim 14 wherein said reference surface is shaped to approximate the surface of the eye to enable the conformable substance to have a thin cross section over the examined portion of the eye.

16. The method of claim 14 wherein said conformable substance contains a constituent which fluoresces when illuminated by selected radiation such that intensity of fluorescent emission from points in said conformable substance are dependent upon the thickness of said conformable substance at said points, said method further including the steps of (a) irradiating said conformable substance, when conformed to said surface of the eye and said reference surface, with incoming and fluorescent radiation passing through said reference member, (b) detecting the intensity of fluorescent radiation emitted from a multiplicity of points over the area of said conformed substance sufficient to represent the topography of said portion of interest, said detection being conducted with a detector that receives fluorescent radiation from said conformed substance through said reference member, and (c) determining from the intensity values over the area of said conformed substance the thickness of the conformed substance at the corresponding points.

17. The method of claim 16 wherein said conformable substance comprises a biologically compatible liquid carrying a bio-compatible fluorescent dye, confined by a biologically compatible barrier exposed to engage the eye.

18. The method of claim 14, 15, or 16 wherein said conformable substance comprises a fluid contained by a pliable barrier supported in a manner to confine said fluid, said barrier having a surface exposed to the eye that is defined by a biologically compatible substance.

19. The method of claim 14, wherein said conformable substance comprises a constituent which substantially absorbs radiation passing through the reference member and is contained within a pliable barrier having a surface exposed to the eye formed by a diffusive reflector reflecting radiation when illuminated, said surface exposed to the eye is defined by a biologically compatible substance.

20. The method of claim 19 wherein said conformable substance substantially absorbs selected radiation such that the intensity of reflected radiation from points in said pliable barrier pressed against the surface of the eye are dependent upon the thickness of said conformable substance at said points, said method further including the steps of (a) irradiating said conformable substance, when conformed to said surface of the eye and said reference surface, with incoming and reflected radiation passing through said reference member, (b) detecting the intensity of said reflected radiation emitted from a multiplicity of points over the area of said pliable barrier sufficient to represent the topography of said portion of interest, said detection being conducted with a detector that receives said reflected radiation from said pliable barrier through said conformable substance and said reference member, and (c) determining from the intensity values over the area of said conformed substance the thickness of the conformed substance at the corresponding points.

21. The method of claim 20 including forming an image of fluorescent radiation received via said reference member and determining energy intensities at points in said image.

22. A method for determining information concerning the topography of a surface of interest of an object comprising (a) providing a reference member having a rigid reference surface directed toward said object, said reference surface being of predetermined shape and said reference member being transparent to radiation, (b) providing between said reference surface and said object a conformable substance contained by a pliable barrier comprising a constituent which fluoresces when illuminated by radiation passing through said reference member, such that intensity of fluorescent emissions from points in said substance are dependent upon the thickness of said substance at said points, (c) pressing said reference member relatively against the surface of said object in the manner that said conformable substance conforms, on one side, to the surface of said object, and on the other side to said reference surface of said reference member, (d) irradiating said conformable substance, when conformed to said object and said reference surface with radiation passing through said reference member, (e) detecting the intensity of fluorescent radiation emitted from a multiplicity of points in said conformable substance sufficient to represent desired information concerning the topography of the surface of interest, said detection being conducted with a detector that receives radiation from said conformable substance through said reference member, and (f) determining the topography of the surface of said abject from thickness data of said conformable substance in reference to said predetermined shape of said reference surface.

23. A method for determining information concerning the topography of a surface of interest of an object comprising (a) providing a reference member having a rigid reference surface directed toward said object, said reference surface being of predetermined shape and said reference member being transparent to radiation, (b) providing between said reference surface and the surface of said object a conformable substance capable of assuming the conformation of surface against which it is engaged, said conformable substance comprising a constituent which substantially absorbs radiation, said constituent being contained within a pliable barrier having a surface exposed to the surface of said object, said barrier being formed by a diffusive reflector, (c) pressing said reference member relatively against the surface of said object in the manner that the conformable substance conforms, on one side, to the surface of said object, and on the other side to said reference surface of said reference member, (d) irradiating said conformable substance, when conformed to the surface of said object and said reference surface with radiation passing through said reference member, (e) detecting the intensity of diffuse radiation from a multiplicity of points distributed over said pliable barrier sufficient to represent desired information concerning the topography of the surface of interest, said detection being conducted with a detector receiving radiation from said multiplicity of points through said reference member, intensities of said radiation being dependent upon the thickness of said conformable substance at the respective points and constituting said thickness data, and (f) determining the topography of the surface of said object from thickness data of said conformable substance in reference to said predetermined shape of said reference surface.

* * * * *